(12) United States Patent
Zhuang et al.

(10) Patent No.: US 8,774,359 B1
(45) Date of Patent: Jul. 8, 2014

(54) GATE STACK METROLOGY

(75) Inventors: Ghuorong V. Zhuang, Santa Clara, CA (US); John Fielden, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 404 days.

(21) Appl. No.: 13/192,611

(22) Filed: Jul. 28, 2011

Related U.S. Application Data

(60) Provisional application No. 61/369,650, filed on Jul. 30, 2010.

(51) Int. Cl.
*G01N 23/20* (2006.01)
(52) U.S. Cl.
USPC .......................................................... 378/70
(58) Field of Classification Search
USPC ................................. 378/44, 70–89
See application file for complete search history.

(56) References Cited

U.S. PATENT DOCUMENTS

| | | | |
|---|---|---|---|
| 3,787,692 A * | 1/1974 | Anderson | 250/305 |
| 7,231,324 B2 | 6/2007 | Orrock et al. | |
| 2007/0010973 A1 | 1/2007 | deCecco et al. | |
| 2007/0069125 A1 | 3/2007 | Schueler et al. | |

OTHER PUBLICATIONS

Tanner et al., "Electronic structure and band alignment at the HfO2/4H-SiC interface," J.Appl.Phys. 101, 034108 (2007).
Jin et al., "Electronic properties ultrathin (Hf)2)x(SiO2)1-x dielectrics on Si (100)," J.Appl.Phys. 102, 053709 (2007).
Yeii et al., "Atomic subshell photoionization cross sections and asymmetry parameters: 1<z<103," Atomic Data and Nuclear Data Tables 32, 1-155 (1985).
Li et al., "Effects of Al addition on the native defects in hafnia," Appl.Phys.Lett. 88, 182903 (2006).
Liu et al., "Development of a vacuum ultraviolet laser-based angle-resolved photoemission system with a superhigh energy resolution better than 1 meV," Rev.Sci.Instrum. 79, 023105 (2008).
Cabuil et al., "Process monitoring and surface characterization with in-line xps metrology," Solid State Technology, pp. 48-51, Oct. (2007).
Rangan et al., "GeOx interface layer reduction upon Al-gate deposition on a HfO2/GeOx/Ge(0001) stack," Appl.Phys. Lett. 92, 172906 (2008).

* cited by examiner

*Primary Examiner* — Courtney Thomas
(74) *Attorney, Agent, or Firm* — Luedeka Neely Group, P.C.; Rick Barnes

(57) ABSTRACT

An x-ray photoelectron spectroscopy apparatus for measuring film stack characteristics, of the type having an x-ray source and an x-ray photoelectron spectroscopy module coupled to a contiguous vacuum environment, including an ultraviolet source and an ultraviolet photoelectron spectroscopy module coupled to the vacuum environment.

20 Claims, 5 Drawing Sheets

GATE STACK METROLOGY

FIELD

This application claims all rights and priority on prior U.S. provisional patent application Ser. No. 61/369,650 filed 2010 Jul. 30. This invention relates to the field of integrated circuit fabrication. More particularly, this invention relates to measuring and monitoring physical parameters of gate and capacitor dielectric stacks for process control at high throughput and high precision.

INTRODUCTION

X-ray photoelectron spectroscopy (XPS) is used to measure the thickness and composition of thin film stacks. This method involves directing x-ray radiation towards the surface of a sample, thereby causing photoelectrons to be emitted from the surface. The kinetic energy of the photoelectrons that are emitted from the surface is related to the both the properties of the x-ray radiation itself, and the properties of the material from which the surface is comprised, as given by the photoelectron equation:

$$h\nu = E_{b(I)} + E_{k(I)},$$

where $E_{b(I)}$ is the binding energy or ionization potential of the $I^{th}$ core electron level of the atom relative to vacuum level, $E_{k(I)}$ is the kinetic energy of the photoelectrons emitted from the $I^{th}$ core level, and $h\nu$ is the mean photon energy of the x-ray radiation. The binding energies are generally unique to each element. Thus, the binding energies that are determined can be used to determine the elemental composition of the surface layers.

Ultraviolet photoelectron spectroscopy (UPS) operates in a manner that is somewhat similar to XPS, except that ultraviolet radiation is used instead of x-ray radiation. The photoelectron equation given above is still applicable, except that the excitation source is ultraviolet radiation with a much lower mean photon energy, $h\nu$. The notation of the equation is modified as given below:

$$h\nu = E_{b(v)} + E_{k(v)},$$

where $E_{b(v)}$ is the binding energy of the valence band (instead of a core electron level) relative to vacuum level, and $E_{k(v)}$ is the kinetic energy of the photoelectrons that are emitted from the valence band (instead of from a core electron level). While XPS provides information about the core electron energy levels of the atoms in the surface of the sample, UPS provides information about the valence electron energy levels of the atoms in the surface of the sample. UPS can be used to determine the valence band edge of materials near the surface of the sample.

XPS has been used to measure composition and thickness of ultra-thin (less than about thirty angstroms thick) high-k gate film stacks (where "high-k" indicates a dielectric constant higher than that of silicon dioxide). For example, the thickness and composition of a hafnium silicate $(HfO_2)_x(SiO_2)_{1-x}$ layer that is formed on top of a silicon layer (or substrate) can be obtained from the difference in the energies of the photoelectrons that are emitted from (1) the silicon in the substrate and (2) the silicon that is bonded to oxygen in the hafnium silicate. This equation is given by:

$$t_{Hf-silicate} = \lambda_{Hf-silicate} \cdot \ln\left[\left(\frac{I_{Hf-silicate}}{I_{Si}}\right) \cdot \left(\frac{I_{Si}^i}{I_{Hf-silicate}^i}\right) + 1\right],$$

where $\lambda_{Hf-silicate}$ is the inelastic electron mean free path of the Si2p (core) photoelectrons in the hafnium silicate layer, $I_{Si}^i$ and $I_{Hf-silicate}^i$ are the signal intensities of the Si2p (core) photoelectrons from the silicon layer and from the hafnium silicate layer, respectively, and $I_{Si}$ and $I_{Hf-silicate}$ are the signal intensities of the Si2p (core) photoelectrons from the silicon layer and the hafnium-silicate layer, respectively, as measured from the hafnium silicate layer on the silicon layer.

As can be seen from the equation, the precision and accuracy of these measurements are closely related to the precision and accuracy of the known (or assumed) stoichiometry of the hafnium silicate layer, because the calculated thickness of the hafnium silicate layer is linearly proportional to the electron inelastic mean free path of the Si2p photoelectrons in the hafnium silicate layer. Thus, the electron inelastic mean free path depends on the stoichiometry of the hafnium silicate layer. The Si2p electron inelastic mean free path is about 28.6 angstroms in silicon dioxide, and varies from about 17.28 angstroms to about 22.8 angstroms in $(HfO_2)_x(SiO_2)_{1-x}$, depending on the value of x. Any uncertainty or variation in x results in commensurate variations in the length of the inelastic mean free path of the photoelectrons used to calculate the thickness of the layer.

One method to estimate the value of x is to acquire spectra of the Hf4f (core) photoelectrons and the Si2p (core) photoelectrons, from which the peak intensities of the Si2p and the Hf4f photoelectrons can be obtained. The stoichiometric parameter x can then be determined. However, this method requires a high energy resolution mode ($\Delta E$=about 0.1 to 0.2 eV) in order to differentiate the Si2p electron energies in the hafnium silicate layer from the Si2p electron energies in the silicon substrate.

Another method to determine x is to acquire spectra of the O1s (core) photoelectrons at a high energy resolution ($\Delta E$=about 0.1 eV) to separately measure the photoelectrons from (1) oxygen bonded to silicon and (2) oxygen bonded to hafnium in the hafnium silicate layer. After deconvolution, the individual components of the O1s core level from $SiO_2$ and $HfO_2$, respectively, are used to calculate the stoichiometric parameter x.

Unfortunately, the data acquisition time that is needed to achieve an acceptable signal-to-noise ratio for either of these two high energy resolution methods is an order of magnitude greater than that which is required by a low energy resolution method (where $\Delta E$=about 1 to 2 eV).

The metrology throughput for high-k applications is ultimately limited by the total data acquisition time for all of the elements that are present. The data acquisition time is highly application dependent. Sensitivity for a high Z element is typically greater than that for a low Z element. Such sensitivity differences stem from interactions between the x-rays and the material, and are, to a first order, proportional to the element sub-shell photo-ionization cross section. This low sensitivity is further compounded by the need to take the measurements in a small area on a patterned integrated circuit substrate. Because readily available x-ray sources have low x-ray brightness, only a low photon flux can be focused into the small target area. This further increases the length of the data acquisition time needed to achieve a good signal-to-noise ratio. Therefore, these methods suffer from low throughput, which limits their usefulness for in-line metrology in high-volume semiconductor manufacturing.

Another limitation of both XPS and UPS is that the photoelectrons generated by these methods must escape from the material being measured in order to be captured. Electrons interact strongly with matter and can typically travel only thirty to fifty angstroms through a solid layer before they are absorbed by that layer. Thus, XPS and UPS typically provide information about only the top thirty angstroms or so of the surface, with some limited information down to a depth of about fifty angstroms. They typically provide no useful quantitative information from depths below about forty or fifty angstroms from the surface.

What is needed, therefore, is a system that reduces problems such as those described above, at least in part.

SUMMARY OF THE CLAIMS

The above and other needs are met by an x-ray photoelectron spectroscopy apparatus for measuring film stack characteristics, of the type having an x-ray source and an x-ray photoelectron spectroscopy module coupled to a contiguous vacuum environment, including an ultraviolet source and an ultraviolet photoelectron spectroscopy module coupled to the vacuum environment.

In some embodiments an optical metrology module is coupled to the vacuum environment, either in place of or in addition to the ultraviolet source and photoelectron spectroscopy module. In some embodiments, the optical metrology module is at least one of a reflectometer and an ellipsometer. Some embodiments include a controller to combine x-ray photoelectron spectroscopy data and optical metrology data to determine the film stack characteristics.

According to another aspect of the invention there is described a method to determine characteristics of a film stack on a substrate by acquiring an ultraviolet photoelectron spectroscopy spectrum of the film stack within a contiguous vacuum environment, determining the band edge of the film stack from the ultraviolet photoelectron spectroscopy spectrum, determining the stoichiometry of the film stack from the band edge, calculating the electron inelastic mean free path of the film stack from the stoichiometry, acquiring an x-ray photoelectron spectroscopy spectrum of the substrate within the contiguous vacuum environment, and determining the film stack thickness from the substrate x-ray photoelectron spectroscopy spectrum and the electron inelastic mean free path of the film stack.

According to yet another aspect of the invention there is described a method to determine characteristics of a film stack on a substrate by acquiring an ultraviolet photoelectron spectroscopy spectrum of the film stack within a contiguous vacuum environment, determining the band edge of the film stack from the ultraviolet photoelectron spectroscopy spectrum, determining the stoichiometry of the film stack from the band edge, acquiring a vacuum ultraviolet photoelectron spectroscopy spectrum of the film stack within the contiguous vacuum environment, iterating the steps of constructing a model of the film stack using an estimated thickness, theorizing a spectrum for the film stack based on the estimated thickness, comparing the theorized spectrum to the measured spectrum, and revising the estimated thickness, until the theorized spectrum matches the measured spectrum to within a desired tolerance, and then reporting the estimated thickness as the actual thickness of the film stack.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Various embodiments of the present invention take advantage of the dependence of the band gap of high-k dielectric materials on composition. For example, the band gap of hafnium silicate, $(HfO_2)_x(SiO_2)_{1-x}$, increases from about 5.5 eV to about 6.6 eV as x decreases from about 0.75 to about 0.25. The valence band is also sensitive to defects in the film. The composition and defects of a gate dielectric film can be determined by measuring the valence band edge shift and the valence state distribution with ultraviolet photoemission spectroscopy. By combining UPS data with XPS data, the thickness and composition measurement results are improved as compared with measurements made individually by XPS or UPS.

Some embodiments of the invention use an optical measurement such as ellipsometry or reflectometry to determine information about a film layer, such as its direct band gap ($E_g$), and combine that information with XPS data. The thickness and composition measurement results from the combined data are more accurate than the measurements made by either XPS or the optical technique alone.

Some embodiments of the invention combine XPS with UPS and another optical measurement technique, such as ellipsometry or reflectometry. The gate dielectric stack energy band offset with respect to silicon can be measured directly by combining a direct band gap ($E_g$) measurement using optical methods (vacuum ultraviolet reflectometry or ellipsometry) and valence band alignment from ultraviolet photoemission measurement.

Construction

Figure 1:
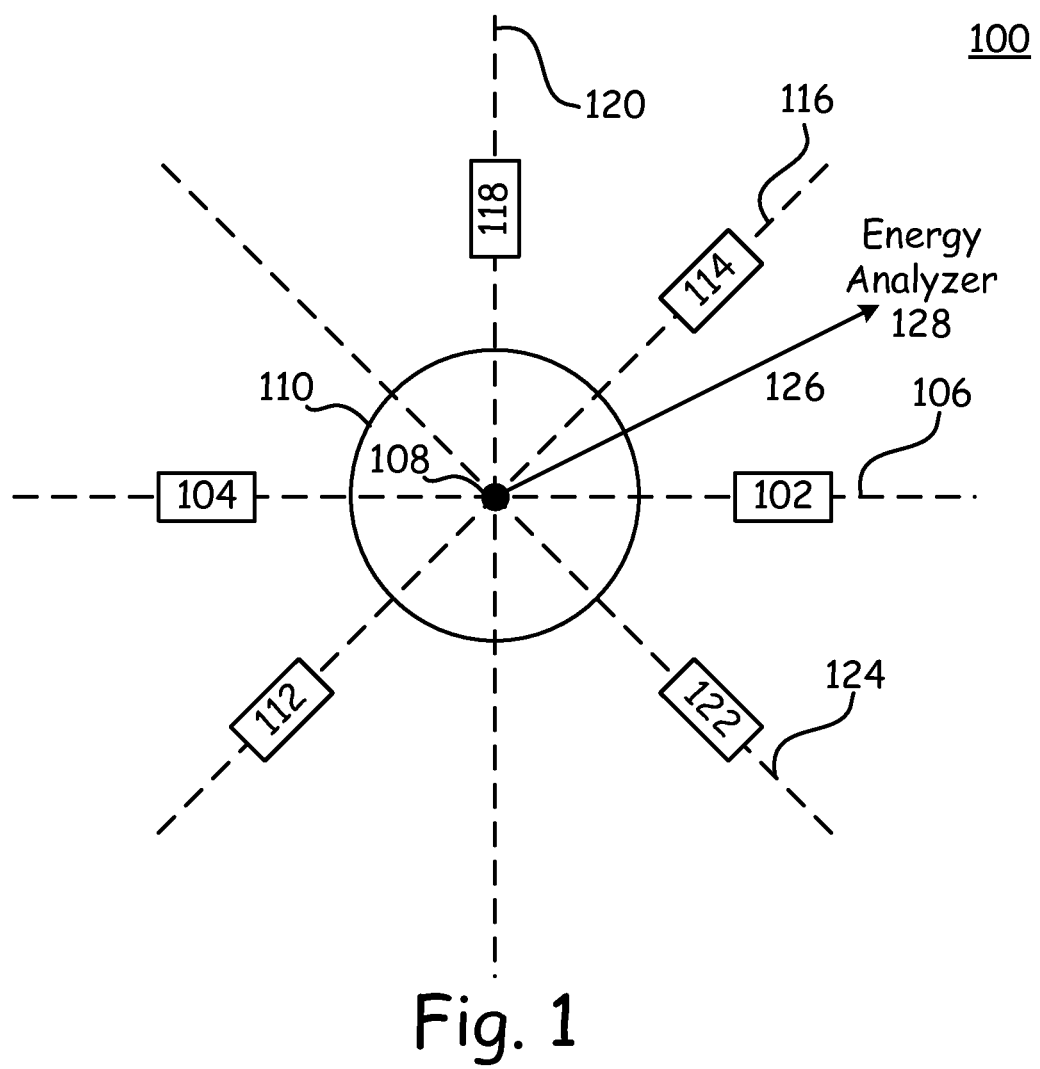
FIG. 1 is a functional block diagram of an apparatus according to an embodiment of the present invention.

With reference now to FIG. 1, there is depicted an apparatus 100 for measuring band gap, thickness, and composition of a thin film stack. The apparatus 100 includes chambers, ports, shielding, pumps, sample staging, valving, electron energy analyzer, instrumentation, and so forth of a standard high vacuum XPS system (not depicted so as to focus with more clarity upon the more novel aspects of the present embodiments), with modifications as described herein.

The apparatus 100 includes an ultraviolet source 102 and an x-ray source 104. In some embodiments, both 102 and 104 are disposed on a common axis 106 through the metrology spot 108 on the sample 110. It is convenient in some embodiments to place the x-ray source 104 and ultra-violet source 102 approximately collinearly in order to provide room for the other components of the system 100.

The x-ray source 104 typically includes an electron gun, electron optics, anode, and x-ray focusing optics. High-energy electrons emitted by the electron gun are focused by the electron optics on the anode in a small spot. The electron optics may also incorporate deflectors for controlling the position where the electrons land on the anode. Either the gun or the electron optics may contain a means for turning off the electron beam or directing the electron beam away from the anode in order to turn off the x-ray radiation. The surface layer of the anode typically includes aluminum or magnesium in order to generate x-rays with an energy of about 1.2 keV to about 1.5 keV. The x-rays are focused by x-ray focusing optics to the metrology spot 108. The x-ray focusing optics may also incorporate an x-ray filter that is highly reflective for the desired x-ray wavelength, and has low reflectivity for other x-ray wavelengths. The x-rays illuminate an area on the sample 110 approximately equal to the area on the anode where the electrons were focused.

The ultra-violet source 102 typically includes an ultraviolet lamp or ultraviolet light source that emits ultraviolet radiation through an aperture. An objective lens focuses the ultraviolet light to the metrology spot 108 on the sample 110. The objective lens may be a Schwarzschild objective or other type of catadioptric or refractive objective suitable for the ultraviolet wavelength used. The ultraviolet source may contain a mechanism for turning the ultraviolet radiation on or off or for blocking the ultraviolet radiation, so that the sample 110 is only illuminated with ultraviolet radiation at the appropriate time.

The ultraviolet radiation that illuminates the sample 110 is substantially monochromatic. Suitable vacuum ultraviolet sources 102 include a gas discharge line source such as the Omicron HIS 13 SPECS UVS300, and a pulsed laser excitation source using a nonlinear optical crystal to generate a high harmonic at an ultraviolet wavelength. The most suitable gases for a lamp are helium, which generates resonance lines such as HeI (21.2 eV) and HeII (40.8 eV), and neon, which generates resonance lines such as NeI (16.7 eV) and NeII (26.9 eV). Other inert gases could be used instead to generate other ultraviolet emission lines. The light source may incorporate a filter to pass substantially only the line of interest and to suppress other emission. Some lamps may be windowless. When the lamp is windowless, the aperture has a diameter of no more than about one hundred microns, which is differentially pumped to maintain vacuum conditions near the sample 110. When the ultra-violet source 102 includes a window, differential pumping may not be needed.

In some embodiments, a single measurement site 108 is used for both UPS and XPS measurements. In other embodiments there is a displacement between the two measurement sites. The small displacement can be determined and the system 100 programmed to automatically move the position of the sample 110 between the different XPS and UPS measurement sites, as desired.

The x-rays from the x-ray source 104 and the ultraviolet radiation from the ultraviolet radiation source 102 both cause photoelectrons 126 to be emitted from the sample 110 in a Z direction, up from the plane of the sample 110. These photoelectrons are collected by an energy analyzer 128 equipped with an electron lens. The electron analyzer 128 in some embodiments is a hemispherical analyzer. A magnet disposed under the sample 110 is used in some embodiments to more efficiently direct photoelectrons towards the analyzer 128. The backside of the sample 110 is grounded in some embodiments to reduce the charge on the sample 110 due to the emission of photoelectrons. Other mechanisms, such as an ion shower or ion gun, are known in the art and may be used to minimize sample 110 charge build-up. A potential difference may be maintained between the input of the electron analyzer and the sample 110 so as to help the electron analyzer capture photoelectrons more efficiently.

In some embodiments a source and illumination optics module 112 is disposed across from collection optics and detector module 114, where both 112 and 114 are disposed on a common axis 116 through the metrology spot 108 on the sample 110. In some embodiments the modules 112 and 114 comprise at least one of a reflectometer and an ellipsometer, operating in one or more of the vacuum ultraviolet, ultraviolet, and visible wavelength ranges. In some embodiments the module 112 is equipped with a broad band vacuum ultraviolet source that has a spectral range that is at least sufficiently broad for measuring both the band gap and the thickness of gate dielectric materials.

In some embodiments, modules 112 and 114 are constructed as follows. A light source directs light towards a polarizer that transmits substantially one polarization state. The light source might be a substantially monochromatic light source such as a laser or a lamp with a strong emission line selected by a filter, or may be a broadband source, such as an arc or discharge lamp covering a broad range of wavelengths. If the light source is polarized, in some embodiments, the polarizer may be omitted. The polarized light is focused onto the metrology spot 108 on the sample 110 by focusing optics, which may comprise a lens, a mirror, or a combination of lenses and mirrors. In some embodiments a compensator (also known as a retarder) converts the polarized radiation to elliptically polarized radiation. The compensator is optional and may not be present in some embodiments. After the light is reflected from the sample 110, it may, optionally, pass through a compensator. The light is collected and focused by focusing optics that may comprise lenses or mirrors that direct the light to a polarizing element, known as an analyzer. The light then passes to a detector, which may comprise a spectrometer when the light source is broadband, but may comprise a photodiode or photomultiplier when the light source is substantially monochromatic. The signal from the detector is passed to a computer for analysis.

In operation, at least one of the polarizer, analyzer or the compensator is rotated to acquire data for different polarization states. Preferably the rotation is a continuous rotation motion, but in some embodiments, the optical element might make several discrete steps rather than a continuous rotation. In some embodiments one of the polarization elements before the sample 110 and one of the polarization elements after the sample 110 may both be rotated simultaneous in order to determine more polarization information about the sample 110.

In some embodiments, all the modules 102, 104, 112, and 114 are disposed in an azimuthal direction, and the apparatus 100 is otherwise configured, such that a pattern recognition optical module 118 disposed along axis 120, a sample height detection optical module 122 disposed along axis 124, and the x-ray source module 104 and vacuum ultraviolet source module 102 disposed along axis 106, all have no obstructions in their measurement paths through the metrology spot 108.

By adding an ultraviolet photoelectron spectroscopy module 102 and an optical metrology module 112/114, the apparatus 100 not only improves gate dielectric metrology throughput by several orders of magnitude, but also extends the capability of the system 100 beyond characterizing just the composition and thickness of a gate dielectric stack. Additionally, the gate dielectric band gap ($E_g$), valence, and conduction band edge offset at the interface and doping-induced interface states are also measurable. Further, the theoretical predicted valence band, with ab initio density functional theory calculation, can be used to predict the physical parameter variation induced valence band change on the gate dielectric stack being measured.

Operation

Figure 2:
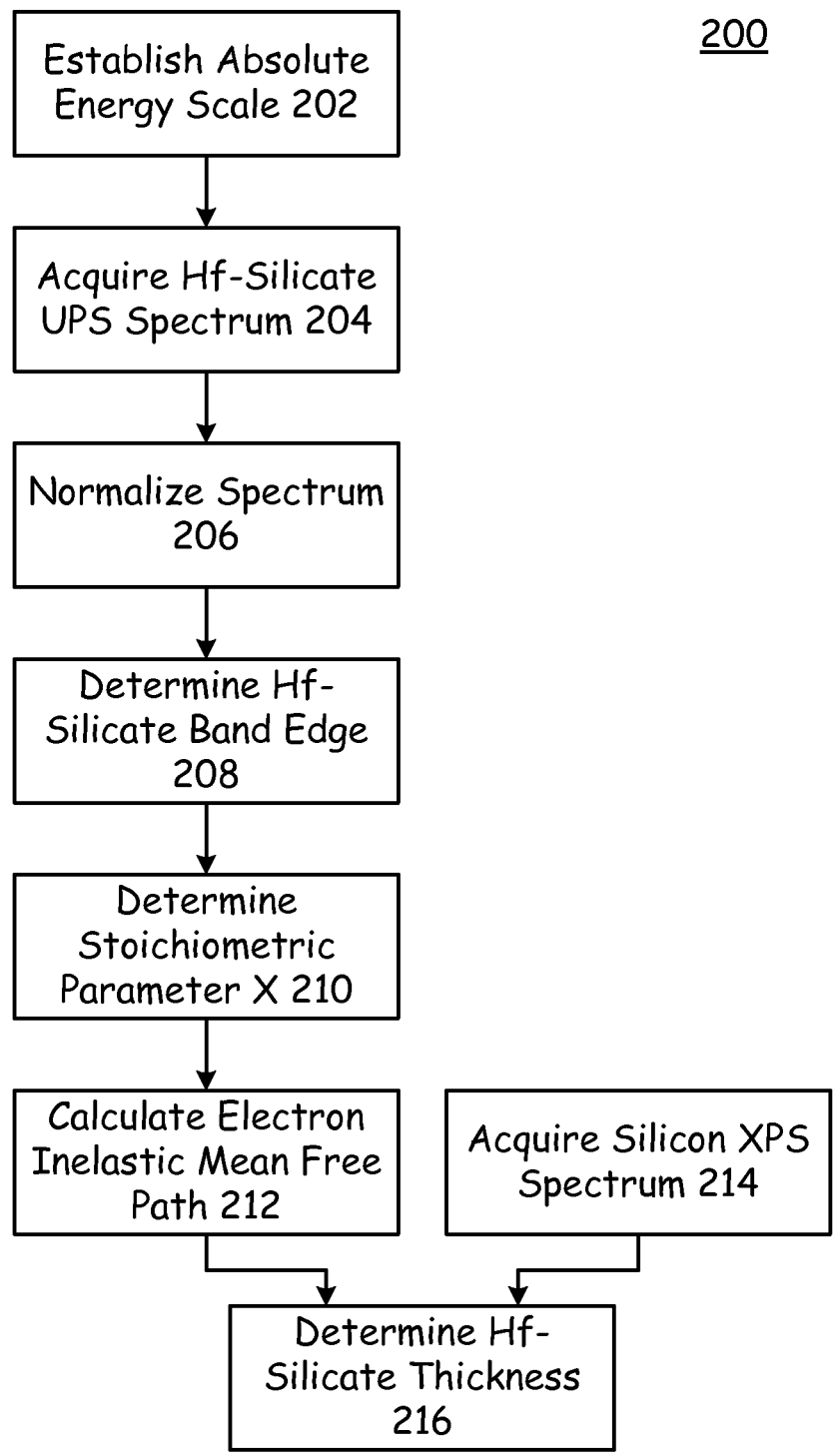
FIG. 2 depicts a flowchart of a method according to a first embodiment of the present invention.

FIG. 2 depicts a flow chart 200 for a first method of operation of the apparatus 100, using a hafnium silicate film stack as an example. However, it is appreciated that the method is applicable to other gate dielectric film stacks. Method 200 can also be used to measure the gate dielectric band offset.

According to the method 200, an absolute binding energy scale is established for the apparatus 100 by measuring a clean surface of a sample 110, formed of a well-characterized material, such as gold, as given in step 202. Since the band edge of gold is well known, the difference between the value determined from the data and the known value can be used to determine an offset of the apparatus 100.

An ultraviolet photoelectron spectroscopy spectrum for the valence band of the sample 110 (such as hafnium silicate) is then acquired, as given in step 204. The ultraviolet photoelectron spectroscopy spectrum is then normalized with respect to the valence band maximum intensity, as given in step 206. The band edge of the sample 110 is then determined, as given in block 208. The stoichiometric parameter x (and hence the composition) of the hafnium silicate sample 110 is then determined from the band edge, as given in block 210. The stoichiometric parameter x is then used to calculate the inelastic mean free path, as given in block 212.

An x-ray photoelectron spectroscopy spectrum is obtained for the silicon core level, as given in block 214, and the hafnium silicate film thickness is determined using the inelastic mean free path, as based on the hafnium silicate film composition and the x-ray photoelectron spectroscopy spectra, as given in block 216.

Figure 3:
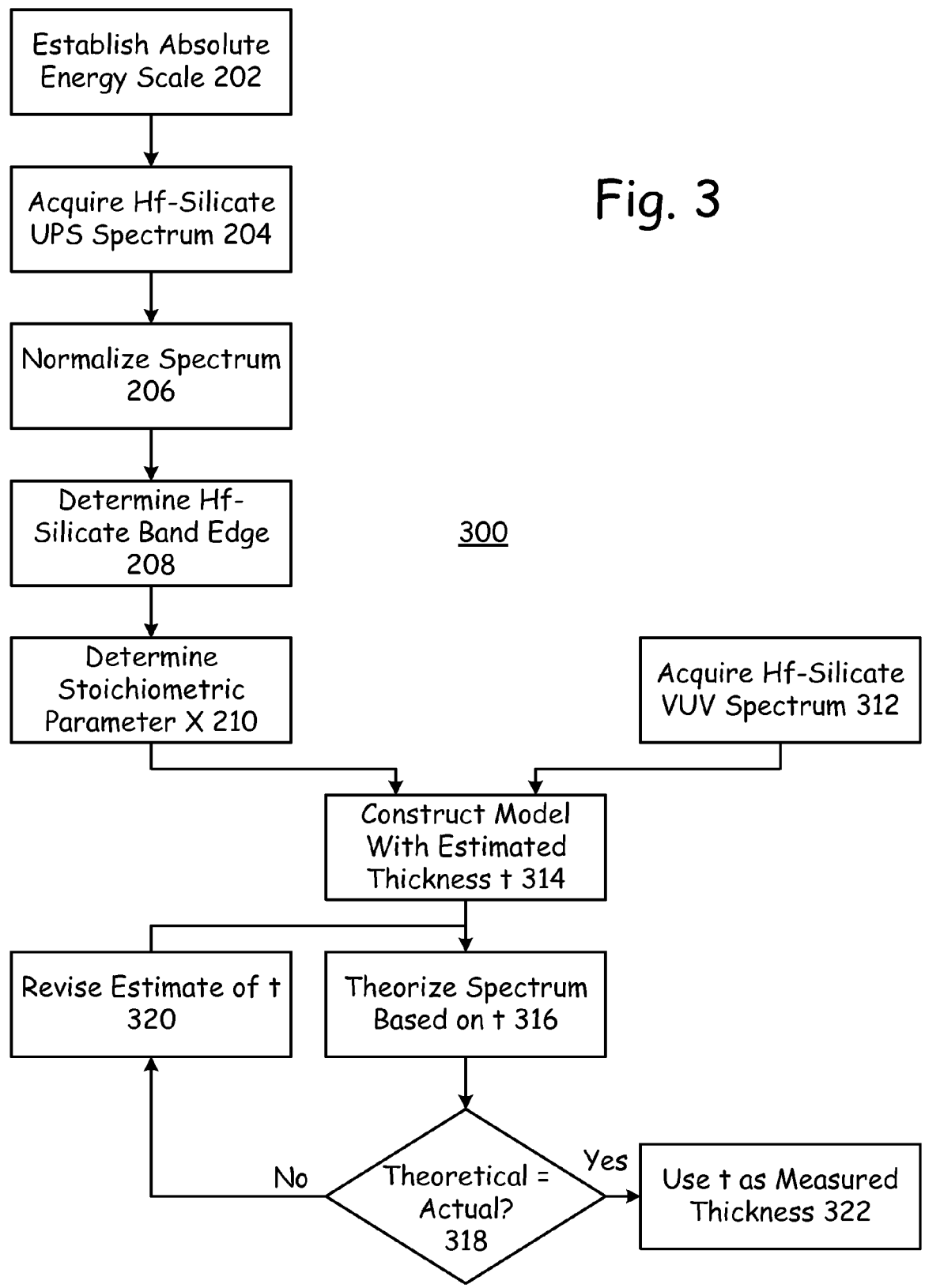
FIG. 3 depicts a flowchart of a method according to a second embodiment of the present invention.

FIG. 3 depicts a flow chart 300 for an alternate method of operation of the apparatus 100. In this method, steps 202, 204, 206, 208 and 210 are the same as for method 200. As shown in block 312, an optical spectrum (such as a vacuum ultraviolet spectrum) is acquired of the hafnium silicate layer under investigation. A film stack model is constructed using the composition parameter x from step 210 and an estimate t of the thickness of the hafnium silicate layer, as given in block 314. The film stack model is used to generate a theoretical optical spectrum, as shown in block 316. In block 318, the theoretical optical spectrum is compared with the measured optical spectrum that was acquired in block 312. If the theoretical spectrum and the measured spectrum match within a predetermined threshold (consistent with the noise and other errors and uncertainty in the data), then t is a good estimate of the thickness, as shown in block 322. If the match is not good enough, then the thickness estimate t is updated as given in block 320, and the process of generating a theoretical spectrum and comparing it to the actual spectrum is repeated until an acceptable match is achieved. The thickness and/or composition results can be reported to the operator.

Figure 5:
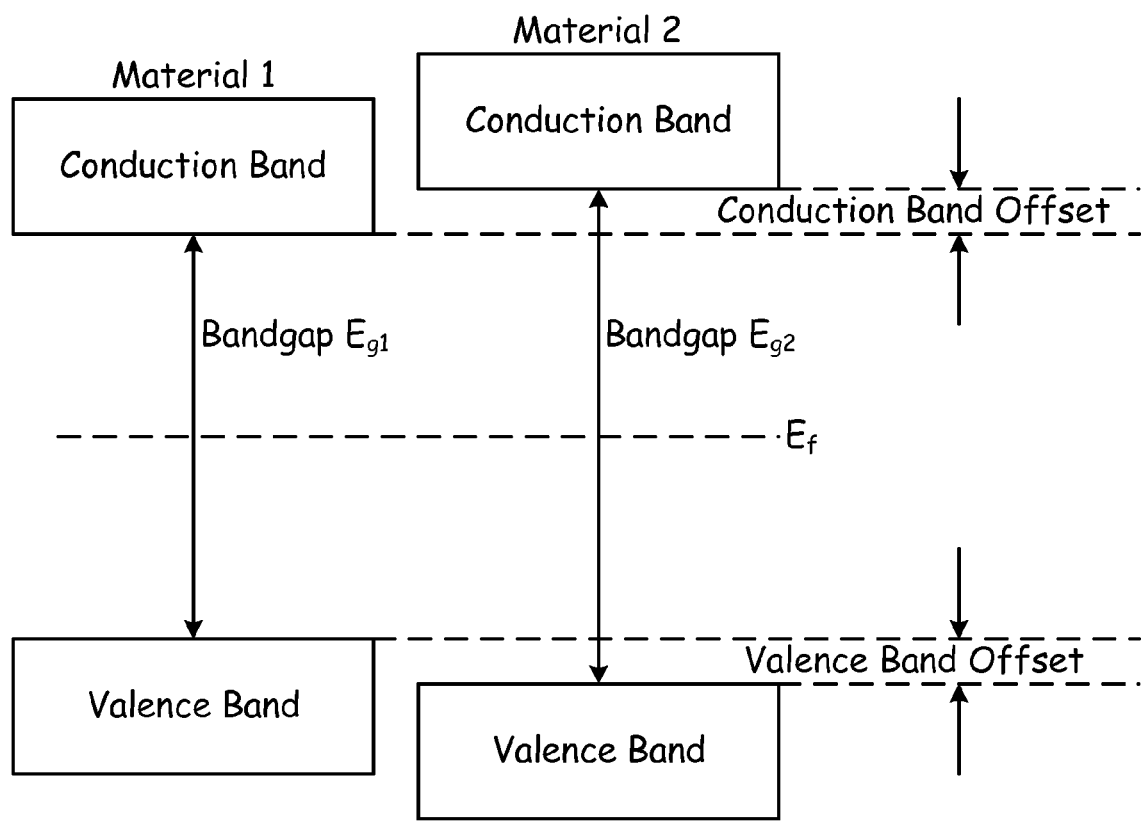
FIG. 5 is an energy diagram showing the definition of the terms band gap and band gap offset in terms of the valence bands and Fermi level.

An important measurement for a gate dielectric layer is the band offset for the gate dielectric layer relative to the silicon band offset. This measurement is especially important for silicon field effect transistors, where the gate dielectric band alignment relative to silicon is used as a measure of the effectiveness of the dielectric layer in reducing leakage current. The apparatus 100 disclosed here can be used to perform dielectric layer band offset metrology. The concept of band offset and a general pictorial description of some of the other terms as used in this disclosure is provide in FIG. 5.

Figure 4:
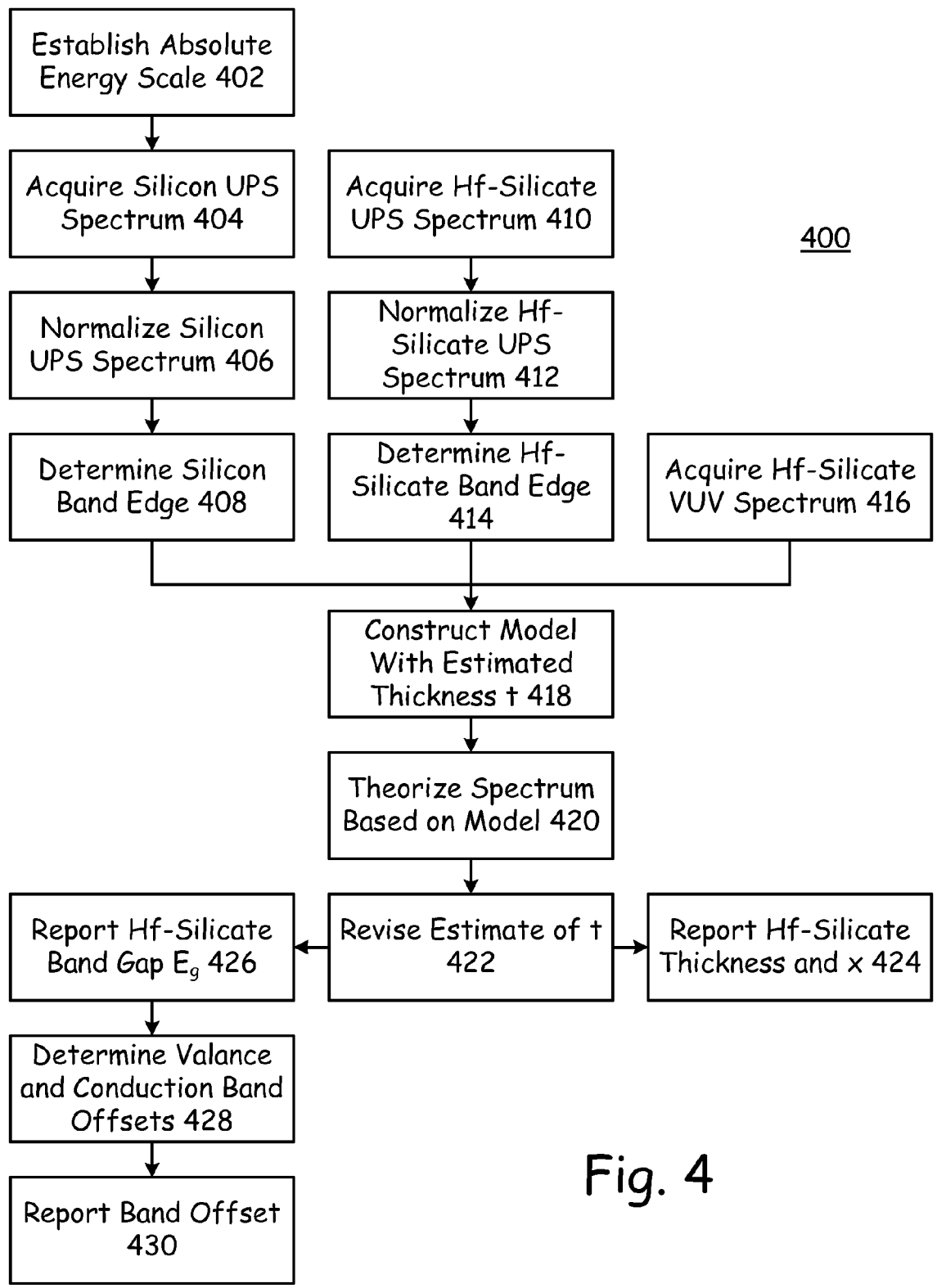
FIG. 4 depicts a flowchart of a method according to a third embodiment of the present invention.

Flow chart 400 in FIG. 4 depicts a method of determining the band offsets for a dielectric stack on a silicon substrate. Several of the steps in method 400 are analogous to the steps as recited in regard to methods 200 and 300 as described above, but are given new numbering in method 400 so as to reduce confusion in the flow of the method 400.

If it has not previously been calibrated, then the UPS is first calibrated with a clean surface of a known material such as gold, as given in block 402 and explained above. Then a UPS spectrum of the silicon substrate is acquired as given in block 404. The UPS spectrum of the silicon substrate is normalized with respect to the valence band maximum intensity, as given in block 406, and the band edge of the silicon substrate is determined as given in block 408. A UPS spectrum is acquired of the film stack, such as a high-k film stack like hafnium-silicate, as given in block 410. This spectrum is also normalized, as given in block 412, and the film stack band edge is determined as given in block 414.

An optical spectrum, such as a vacuum ultraviolet spectrum, is acquired for the film stack, as given in block 416, and is analyzed as given in blocks 418, 420, and 422, in a manner similar to that described above for method 300. In block 418, a film stack model is constructed using the composition parameter x, based on the XPS and UPS spectra and the thickness estimate t, as described above. In block 420, the theoretical optical spectrum is generated, based on the model. The estimate of t is varied, as given in block 422, until the theoretical spectrum matches the acquired VUV optical spectrum within a given tolerance.

One result of this processing is the thickness of the high-k layer, which is reported as given in block 424. Another result of this processing is the band gap $E_g$ of the high-k material, which is fed forward as shown at block 426 into block 428. In block 428 the band gap of the high-k material is combined with the known band gap of the substrate and the measured band edges of the substrate and high-k layer to compute the band offset between the high-k layer and the substrate. The band offset is reported as shown in block 430.

A high brightness ultraviolet source 102 enables the system 100 to acquire valence band spectra (using UPS) in just a few seconds as compared to the tens or hundreds of seconds required by core-level spectra (XPS). The UPS 102 has more surface sensitivity due to a combination of the small penetration depth of the ultraviolet source 102 and the low energy photoelectron small inelastic mean free path. Therefore, UPS is more sensitive to the film stack and provides a fast and simple method to determine the composition of a high-k film stack, without the photoelectron interference from the silicon substrate that occurs in XPS. Although probing the material valence band is possible with XPS, the sensitivity and data acquisition time are severely limited by the photo-ionization cross-section at excitation energies of 1253.6 eV (Magnesium Kα) and 1486.6 eV (Aluminum Kα), the two x-ray sources most-commonly used for XPS. Additionally, UPS provides the valence band edge alignment/offset of the high-k film with respect to the Fermi level, substrate (silicon, germanium, etc.), and other buffer layers or standards, such as silicon oxide.

In various embodiments, the high-k films described herein comprise one or more of oxides or nitrides of aluminum, hafnium, zirconium, silicon, or rare earth metals such as lanthanum and lutetium. One or more of the layers can be doped with nitrogen. The high-k film stack can comprise multiple layers of different materials, and be used as a gate dielectric or a capacitor dielectric film. The methods and apparatus described herein are also applicable to measuring thickness and composition of thin semi-metallic materials, such as titanium nitride or metal silicides.

Although the above examples use silicon as the substrate material upon which the layers to be measured are deposited, it is appreciated that the methods and apparatus described herein can be used to make measurements on other substrate materials, including but not limited to germanium, gallium arsenide, gallium nitride, and other III-V materials.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. In an x-ray photoelectron spectroscopy apparatus for measuring film stack characteristics, of the type having an x-ray source and an x-ray photoelectron spectroscopy module coupled to a contiguous vacuum environment, the improvement comprising:
   an ultraviolet source coupled to the vacuum environment, and
   an ultraviolet photoelectron spectroscopy module coupled to the vacuum environment,
   where the ultraviolet source and the x-ray source are positioned to inspect a common side of the film stack.

2. The apparatus of claim 1, further comprising an optical metrology module coupled to the vacuum environment.

3. The apparatus of claim 1, wherein the film stack is a high-k film stack.

4. The apparatus of claim 1, wherein the film stack is hafnium silicate.

5. The apparatus of claim 1, wherein the characteristics include at least one of film stack thickness and film stack stoichiometry.

6. In an x-ray photoelectron spectroscopy apparatus for measuring film stack characteristics, of the type having an x-ray source and an x-ray photoelectron spectroscopy module coupled to a contiguous vacuum environment, the improvement comprising an optical metrology module coupled to the vacuum environment, where the optical metrology module and the x-ray source are positioned to inspect a common side of the film stack.

7. The apparatus of claim 6, wherein the optical metrology module comprises at least one of a reflectometer and an ellipsometer.

8. The apparatus of claim 6, further comprising a controller to combine x-ray photoelectron spectroscopy data and optical metrology data to determine the film stack characteristics.

9. The apparatus of claim 6, wherein the film stack is a high-k film stack.

10. The apparatus of claim 6, wherein the characteristics include at least one of film stack thickness and film stack stoichiometry.

11. A method to determine characteristics of a film stack on a substrate, the method comprising the steps of:
    acquiring an ultraviolet photoelectron spectroscopy spectrum of the film stack within a contiguous vacuum environment,
    determining the band edge of the film stack from the ultraviolet photoelectron spectroscopy spectrum,
    determining the stoichiometry of the film stack from the band edge,
    calculating the electron inelastic mean free path of the film stack from the stoichiometry,
    acquiring an x-ray photoelectron spectroscopy spectrum of the substrate within the contiguous vacuum environment, and
    determining the film stack thickness from the substrate x-ray photoelectron spectroscopy spectrum and the electron inelastic mean free path of the film stack.

12. The method of claim 11, wherein the substrate is a silicon substrate.

13. The method of claim 11, wherein the film stack is a high-k film stack.

14. The method of claim 11, wherein the film stack is hafnium silicate.

15. The method of claim 11, wherein the characteristics include at least one of film stack thickness and film stack stoichiometry.

16. A method to determine characteristics of a film stack on a substrate, the method comprising the steps of:
    acquiring an ultraviolet photoelectron spectroscopy spectrum of the film stack within a contiguous vacuum environment,
    determining the band edge of the film stack from the ultraviolet photoelectron spectroscopy spectrum,
    determining the stoichiometry of the film stack from the band edge,
    acquiring a vacuum ultraviolet photoelectron spectroscopy spectrum of the film stack within the contiguous vacuum environment,
    iterating the steps of,
       constructing a model of the film stack using an estimated thickness,
       theorizing a spectrum for the film stack based on the estimated thickness,
       comparing the theorized spectrum to the measured spectrum, and
       revising the estimated thickness,
    until the theorized spectrum matches the measured spectrum to within a desired tolerance, and
    reporting the estimated thickness as the actual thickness of the film stack.

17. The method of claim 16, wherein the substrate is a silicon substrate.

18. The method of claim 16, wherein the film stack is a high-k film stack.

19. The method of claim 16, wherein the film stack is hafnium silicate.

20. The method of claim 16, wherein the characteristics include at least one of film stack thickness and film stack stoichiometry.

* * * * *